US006348212B2

(12) United States Patent
Hymes et al.

(10) Patent No.: US 6,348,212 B2
(45) Date of Patent: *Feb. 19, 2002

(54) TREATING TRAUMATIC BURNS OR BLISTERS OF THE SKIN

(75) Inventors: Alan C. Hymes, Mount Vernon, WA (US); Jane Nichols, Bloomington, MN (US)

(73) Assignee: LecTec Corporation, Minnetonka, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,271

(22) Filed: May 18, 1999

(51) Int. Cl.[7] .............................. A61F 9/70; A61K 13/00
(52) U.S. Cl. ...................... 424/449; 424/443; 424/446; 424/448; 424/400; 424/78.02; 424/78.06
(58) Field of Search .................................. 424/400, 405, 424/443, 444, 445, 446, 447, 448, 485, 78.02, 78.06; 206/461, 462, 463, 464, 466

(56) References Cited

U.S. PATENT DOCUMENTS

| | | |
|---|---|---|
| 4,306,551 A | 12/1981 | Hymes et al. |
| 4,307,717 A | 12/1981 | Hymes et al. |
| 4,622,089 A | 11/1986 | Lauritzen |
| 4,671,266 A | 6/1987 | Lengyel |
| 4,675,009 A | 6/1987 | Hymes et al. |
| 5,476,443 A | 12/1995 | Cartmell et al. |
| 5,489,262 A | 2/1996 | Cartmell et al. |
| 5,501,661 A | 3/1996 | Cartmell et al. |
| 5,536,263 A | 7/1996 | Rolf et al. |
| 5,547,681 A | 8/1996 | Clark et al. |
| 5,643,589 A | 7/1997 | Chalmers |
| 6,039,940 A | * 3/2000 | Perrault et al. .......... 424/78.06 |

FOREIGN PATENT DOCUMENTS

WO   WO 97/48387   12/1997

OTHER PUBLICATIONS

Holum (1995), Elements of General, Organic, and Biological Chemistry, Ninth Edition, pp. 136–138.*

* cited by examiner

*Primary Examiner*—Dameron L. Jones
(74) *Attorney, Agent, or Firm*—Schwegman, Lundberg Woessner & Kluth, P.A.

(57) ABSTRACT

Blisters of the skin are treated by applying to the skin over the blister a flexible moisture-containing hydrophilic hydrogel patch that includes a backing support such as paper, cloth or plastic and a water-based hydrogel layer applied to the backing. The hydrogel layer comprises a hydrophilic natural or synthetic polymer to provide body dispersed in water and can be a tacky adhesive. The polymer can comprise any high molecular weight hydrophilic carbohydrate such as karaya, cornstarch, or a kelp gel and/or a synthetic hydrophilic polymer such as polyacrylamide or polyacrylic acid. A humectant such as a polyhydric alcohol, keeps the gel layer moist. A solute such as salt, protein, sugar or an alcohol is dissolved in the water in a quantity sufficient to raise the osmotic pressure enough to maintain the hydrogel layer in a hypertonic state with respect to the blister. The hydrogel which hydrates the normally dry upper layer of skin forms a hydrophilic bridge with the patient's skin that allows fluid to be drawn by osmotic pressure from the blister through the normally dry stratum corneum into the patch. In addition, the hydrogel very quickly significantly dimishes the pain secondary to skin burns and blisters.

42 Claims, 3 Drawing Sheets

TREATING TRAUMATIC BURNS OR BLISTERS OF THE SKIN

FIELD OF THE INVENTION

This invention relates to a method and therapeutic adhesive patch product for treating trauma blisters, burns or exposure to chemicals.

BACKGROUND OF THE INVENTION

Blisters of the skin can be caused by repeated trauma due to chafing against the skin, most commonly experienced on the hands and feet or from other causes. Further, some first and second degree burns of the skin or exposure to chemicals can also cause blisters. These blisters all have a common pathology regardless of the traumatic causation.

When the epidermal layer of the skin is traumatized, an acute accumulation of clear extracellular fluid develops very rapidly between the epidermal and dermal layers of the skin. Secondary inflammation then occurs as part of the healing process. If the epidermal layer opens, the secondary inflammation also may be associated with infection and, as a result, may develop purulent fluid with an infiltration of white blood cells. Moreover, the actual exposure of the dermal layer of skin often results in pain. The present invention takes advantage of the finding that all of these symptoms can be alleviated in whole or in part by significantly reducing the fluid in the acute stage of the blister while maintaining the integrity of the epidermis.

Immediately following a burn to the skin which results in a first or second degree burn, there is an acute inflammatory reaction in the burned skin consisting of acute dilation of blood vessels with leakage of fluid into the extravascular and extracellular space in the burned skin. In addition, in second degree burns there is characteristically a blister filled with clear fluid on the skin surface. Further, there is a great deal of pain in the injured area which may last up to seven days or more.

In view of the deficiencies in prior treatment, it is an important object of the present invention to provide a treatment for blisters that is safe and can be used by the patient for effectively relieving adverse symptoms or improving the blistered skin and in reducing or eliminating the associated pain.

Another object is to provide an adhesive patch for treating blisters.

These and other more detailed and specific objects of the present invention will be better understood by reference to the following figures and detailed description which illustrate by way of example of but a few of the various forms of the invention within the scope of the appended claims.

SUMMARY OF THE INVENTION

This invention provides a moist and flexible hydrogel, most preferably in the form of a flexible but dimensionably stable patch for covering the blister by which the fluid volume within the skin blister is significantly reduced. This reduction results from placing a hypertonic hydrogel layer in direct contact with the blister so as to produce an osmotic imbalance between the liquid within the blister and the hydrogel. After the patch has been applied, the fluid is drawn out of the blister by osmotic force through the raised epidermis which, upon being hydrated externally by the gel, can then act as a semi-permeable membrane. The structural integrity of the epidermis remains intact due to the protection provided by the patch. Following this, the epidermis will lay down on the dermis. It was found that the epidermis will then heal to the dermis without pain like a split thickness skin graft. Thus, the present invention provides a means of reducing accumulated extracellular fluid contained in the blister. The osmotic imbalance persists while the patch is in place and continues to draw fluid from the low concentration in the blistered skin to the high concentration in the hypertonic hydrogel. This invention therefore concerns a method for treating blistered skin by applying directly to the blistered area a moist, flexible, hypertonic hydrophilic gel patch. While not essential, the gel preferably has a tacky, i.e., pressure-sensitive adhesive, surface enabling the patch to be self-bonding to the skin. This bond enhances hydration of the skin and the transfer of fluids. The patch also includes a backing such as paper, cloth or plastic that acts as a support for the patch and a water-based hypertonic hydrogel layer applied to the backing. The tacky pressure-sensitive adhesive surface of the gel layer, when present, bonds the hydrogel and the patch itself to the skin. The hydrogel layer forms a water bridge between itself and the outer surface of the skin that makes up the top of the blister. This hydro bridge allows the flow of fluid from within the blister, which has a lower osmotic pressure than the osmotic pressure in the hydrogel layer.

The hydrogel layer comprises water and, as a thickening or gel forming agent, a hydrophilic natural or synthetic polymer dispersed in the water. The polymer can comprise a high molecular weight hydrophilic carbohydrate such as karaya, cornstarch, or kelp gel and/or a synthetic hydrophilic polymer such as polyacrylamide, a polyionic gel, or polyacrylic acid. A humectant such as an alcohol containing two or more hydroxyl groups, i.e., a polyhydric alcohol, is preferably employed to keep the adhesive layer moist. Any water soluble solute such as salt or an alcohol is dissolved in the water in a quantity sufficient to raise the osmotic pressure above that within the blister; namely, to a value over about 308 mOsmol/L so as to maintain the adhesive hydrogel layer in a hypertonic state with respect to the interior of the blister. As already noted, the adhesive hydrates the outermost layer of skin above the blister. Consequently, the hydrogel adhesive, when applied to a patient, forms a hydrophilic bridge with the patient's normally dry outer skin layer, the stratum corneum, which allows fluid transport between the skin and the patch across the hydrophilic bridge. With the patch in place on the skin, the fluid in the blister is then transported to the hydrogel layer by osmotic pressure to thereby improve or entirely relieve the blistered condition. After the fluid is gone, the epidermis will then heal to the dermis, much like a split thickness skin graft and without pain. It was also found that the invention provides substantial and sometimes complete removal of pain as soon as it is applied, probably because of its cooling effect since the patch acts somewhat like a heat sink in very good thermal contact with the skin with moisture evaporating from its upper surface.

Another aspect of the invention is the hypertonic moisture-containing adhesive patch itself. The patch as noted above contains a flexible backing and a lower hydrophilic, pressure-sensitive adhesive layer containing water, a hydrophilic polymer dispersed in the water, and a dissolved substance. The relative amounts of the solute and solvent are adjusted such that the osmotic pressure of the patch is above that of the underlying tissue of the patient so as to maintain the adhesive hydrogel layer in a hypertonic state with respect to the fluid in the blister. The tacky surface of the adhesive layer wets the normally dry skin surface and creates the hydrophilic bridge with the patient's elevated skin layer. This allows the free transport of fluid from the blister.

DETAILED DESCRIPTION OF THE INVENTION

Figure 1:
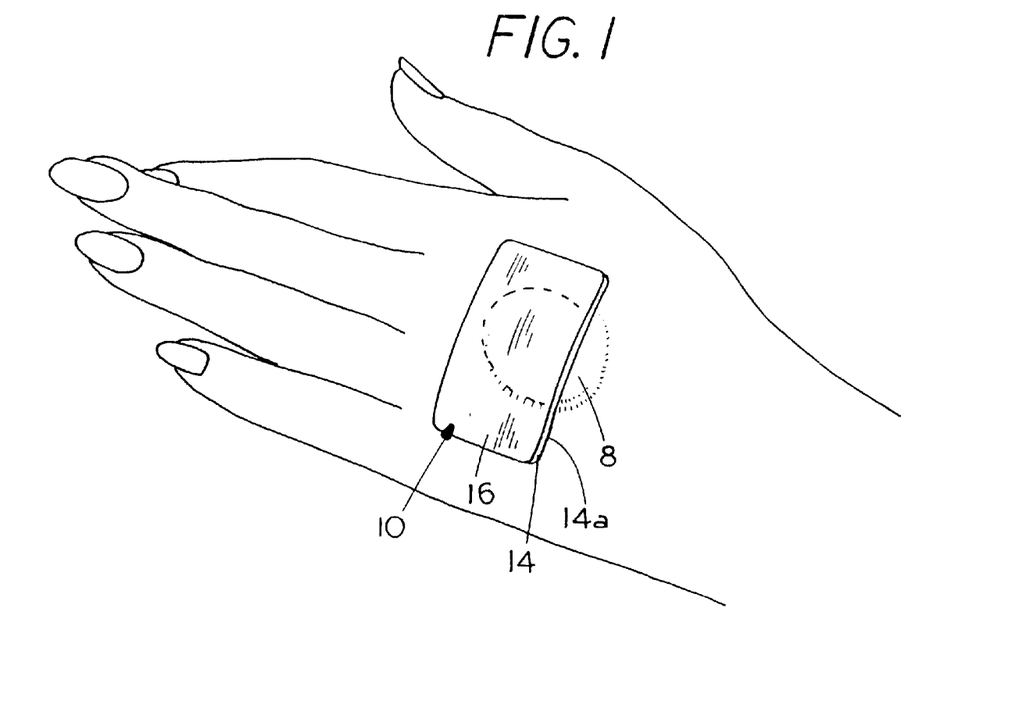
FIG. 1 is a perspective view of the back of the hand showing a patch according to the present invention that has been applied to cover a blister and the surrounding skin.

In FIG. 1 is shown a patient's hand having a blister 8 to which a patch 10 in accordance with the invention has been applied. The patch 10, which in this case is rectangular, has a water-based hydrogel adhesive layer 14 with a pressure-sensitive surface 14a and a backing layer 16 that provides structural support for the patch and is composed, for example, of cloth, nonwoven fabric, or plastic film. The adhesive layer 14 contains moisture and a dissolved material in sufficient quantity to maintain the osmotic pressure within the patch 10 above that of blister beneath the upper layer of skin (the stratum corneum). During use, the patch 10 is bonded to the skin of the patient by the hydrogel adhesive layer 14 directly over the blister 8 being treated. The hydrogel layer 14 contains enough moisture to hydrate the skin, and the tacky surface 14a of the patch 10 forms hydrophilic bridge with the patient's skin by wetting the normally dry stratum corneum 24 (FIG. 4A) enough to allow the progressive transfer of fluid into the adhesive layer 14 through the stratum corneum which acts as a semipermeable membrane when hydrated. The patch 10 is left in place for as long as needed, e.g., a day or more, and is replaced whenever necessary. One preferred protocol is to replace the patch 10 twice a day.

Figure 2:
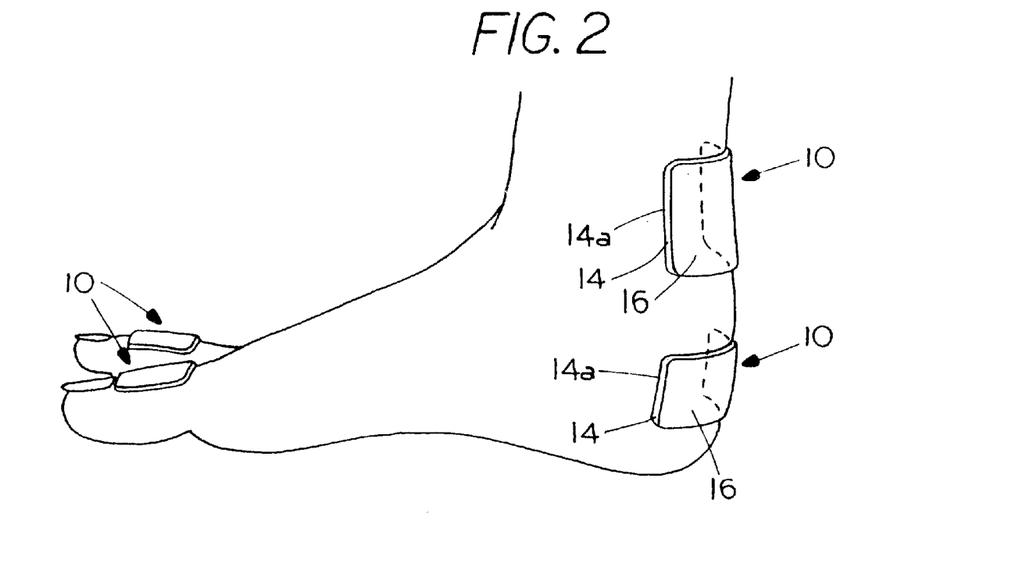
FIG. 2 is a side perspective view of the foot of a patient that has four blisters which are covered by rectangular hypertonic adhesive patches in accordance with the invention.

FIG. 2 shows four more patches 10 which are similar to the patch of FIG. 1. The patches 10 of FIG. 2 are applied to the patient's foot over blisters (not shown) above the heel and on the tops of the toes.

Figure 3:
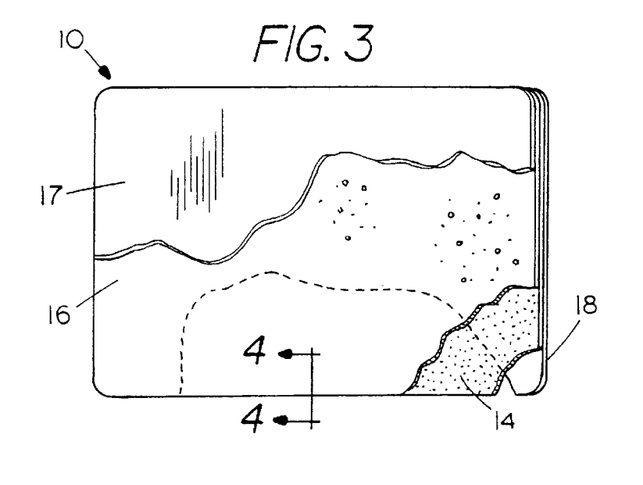
FIG. 3 is a top perspective top view of the patch of FIG. 2 showing a portion of the removable liner that covers the adhesive before the patch is used.
Figure 4:
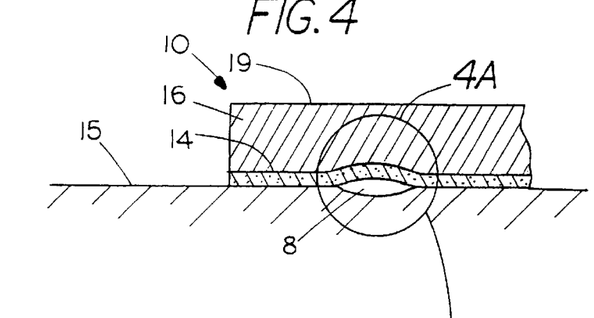
FIG. 4 is a greatly enlarged partial cross-sectional view of the patch taken on line 4—4 of FIG. 3 showing the patch as it appears when applied to the patient's skin over a blister.
Figure 4A:
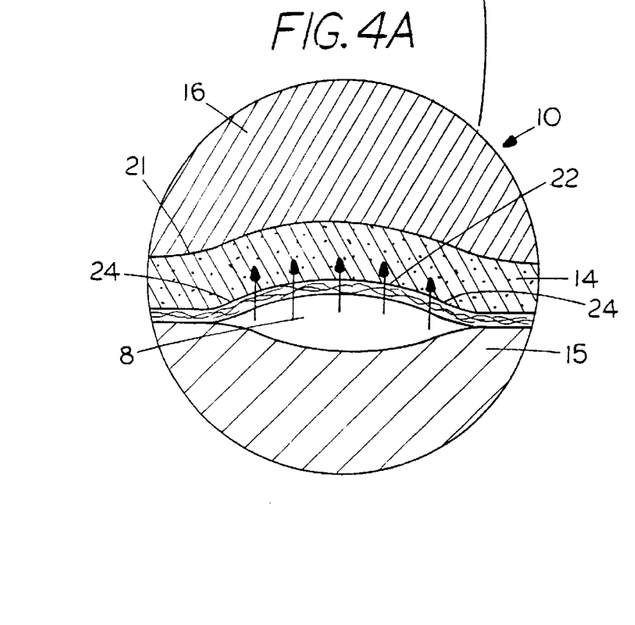
FIG. 4A is a still further enlarged microscopic view showing the lower portion of the patch in contact with the skin over a blister.
Figure 5:
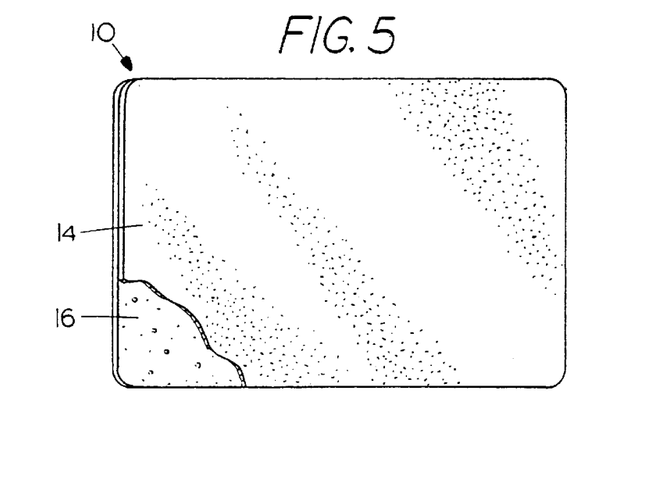
FIG. 5 is a perspective bottom view of the patch of FIG. 3 showing the exposed pressure-sensitive surface after the liner sheet has been removed and before the patch has been applied to the skin.

Refer now to FIGS. 3–4A which illustrate the structural features of the patch in more detail. The patch 10 in this case is provided with an underlying layer of medical grade, non-irritating, hydrated pressure-sensitive adhesive 14 of any suitable type known to those skilled in the art, for example as described in U.S. Pat. Nos. 5,536,263; 4,675,009; 2,498,338; 3,645,835; 4,427,737 and 4,867,150 (which are incorporated herein by reference) except that the osmotic pressure of the adhesive gel is controlled as already described by regulating the ratio of solvent (water) to dissolved solutes. The lower surface 14a of adhesive 14 is protected during shipment and storage by a removable liner sheet 18 (FIG. 3) that can comprise any suitable commercially available release paper or plastic film. The liner sheet 18 can be a 2 mil. sheet of polyester film. Before use, the liner sheet 18 is removed to expose the lower surface of the pressure-sensitive adhesive 14. The patch 10 is then applied to the skin 15 and is held in place by the pressure-sensitive adhesive surface 14a, for example, on the hand or foot of the patient as shown in FIGS. 1, 2, 4 and 4A. While it is preferred that the hydrogel layer have a pressure-sensitive adhesive surface 14a that will hold the patch in contact with the skin 15, the patch 10 can also be held in place if desired by wrapping it with a cloth bandage or by taping down the edges with any suitable commercially available medical adhesive tape (not shown).

The patch 10 is typically about one inch long by one or two inches wide and has rounded corners. It can also be circular with a diameter of from about ½ inch to 1½ inches. The backing sheet 16 typically has a thickness of about 3–8 mils and has applied to it about 0.012 ounces per square inch of the adhesive. The backing sheet 16 is typically a flexible sheet of open-cell polyurethane foam, open-cell polyethylene foam, nonwoven fabric or cloth.

The composition of a preferred hydrogel adhesive 14 will now be described in more detail. The hydrogel layer 14 comprises a base or matrix composed of water and a water-dispersible hydrophilic polymer. The liquid phase of the matrix preferably consists of hydric alcohols such as glycerol and/or propylene glycol, and/or water. The hydrophilic polymer contained in the adhesive layer 14 acts as a thickening or gel forming agent that helps the adhesive layer set up once applied to the backing 16. For this purpose, a high molecular weight natural or synthetic polymer and optionally a polymeric tackifier is included as a part of the hydrophilic hydrogel adhesive layer. The hydrophilic polymer can be any natural or synthetic polymer, for example a gum, i.e., a natural plant exudate such as karaya as described in U.S. Pat. No. 5,536,263 which is incorporated herein by reference, starch, kelp, gum or a synthetic hydrophilic polymer such as polyacrylamide, polyacrylic acid or a polyionic gel, e.g., polysodium acrylate, a polyquaternary amine, a polysulfonate, carboxymethyl cellulose (CMC), carboxypropyl cellulose (CPC), and the like as described in U.S. Pat. No. 5,547,681 which is also incorporated herein by reference. When karaya is used as a thickening or gel forming agent for the hydrogel adhesive layer 14, it has the advantage of providing a bacteriostatic action and thereby reduces bacterial counts. Another advantage of the invention is its ability to prevent infections.

In order to create the desired osmotic pressure within the patch 10, at least one substance is dissolved in the adhesive hydrogel layer 14. Increasing amounts of this solute will create higher osmotic pressures, since the osmotic pressure of a solution is proportional to the fraction of solute molecules in the solution. Enough solute is used to produce an osmotic pressure greater than that of human tissue, namely over about 308 mOsmol/L. Various solutes can be employed. The most suitable for the present invention comprise soluble carbohydrates including sugar, soluble salts, weak acids and bases, mono- and polyhydric alcohols, soluble amino acids or proteins, and other water soluble molecules. Those proteins that are soluble in water form colloidal solutions. On a weight basis, salts are generally the most effective osmotic enhancers since, at the same temperature, equal volumes of solutions showing the same osmotic pressure contain equal numbers of molecules of the solute. If sucrose which has a molecular weight of 342.3 is used, for example, the osmotic pressure of a molal solution is 24.8 atmospheres at 0° C. Sodium chloride, however, with a molecular weight of 58 is almost six times as effective in increasing the osmotic pressure as the same quantity of sucrose by weight. A few examples of the salts that can be employed are sodium chloride, potassium chloride, calcium chloride, and calcium carbonate. Among the sugars that can be used are sucrose, glucose, levulose, and lactose. Among the weak acids that can be employed are acetic acid, adipic acid, aspartic acid, glutamic acid, and malic acid. Among the weak bases are potassium bicarbonate and sodium bicarbonate. Among the proteins are albumin and casein. Among the amino acids are glycine, alanine, cysteine and leucine. Among the alcohols are ethanol, methanol, glycerin, ethylene glycol, and propylene glycol. Other solutes that can be used will be apparent to those skilled in the art. Naturally, the solute should be non-irritating and unlikely to produce toxic reactions or skin irritation at the concentration used. While amounts will vary depending upon the desired osmotic pressure, salts, if used, are typically present for example at concentrations of about 0.1% to 15% by weight or more, and preferably from about 0.5% to about 7% by weight, to produce an osmotic pressure greater than the fluid within the infected skin. Sugars and proteins are typically used in an amount, for example, from about 1% to 25% by weight.

Solutes can be used in combination. For example, the osmotic pressure increase produced by glycerin can be further increased by the addition of any nontoxic electrolyte, e.g., the addition of 1% sodium chloride. A solution of about 0.9% sodium chloride is isotonic with serum or blood. Accordingly, anything with a higher osmotic pressure than the equivalent of 0.9% sodium chloride is sufficient to be at a greater osmotic pressure than blood or serum. However, in practice it is desirable to have a much higher osmotic pressure in the hydrophilic layer than in the blister, since the higher the osmotic pressure of the hydrophilic layer, the greater will be the absorption of moisture from the blister. Moreover, since the permeability of any particular skin area cannot be precisely predicted, it is desirable to keep the osmotic pressure in the adhesive substantially higher than that of the blister to maintain a high osmotic differential and to provide a margin of error. During use, as water is transported from the blister into the hydrophilic adhesive layer of the patch, some electrolytes are carried with it, as well as other substances such as small amounts of simple proteins. The water that thus passes through the stratum corneum, which has been hydrated by the patch, dilutes the salt present in the overlying adhesive layer. As the patch 10 is used, dilution of the solute causes the patch to lose effectiveness over time. Consequently, the patch 10 should be removed periodically and replaced with a fresh patch.

The pressure-sensitive hydrocolloidal adhesive layer 14 can be prepared by admixing the constituents just prior to applying the adhesive to the backing 16. Mixing can be accomplished by providing a processing mixer with a cooling jacket through which a coolant such as a chilled mixture of water and ethylene glycol is passed during operation. The components of the hydrogel are continuously added to the mixer during operation. While any suitable mixer can be used, one suitable mixer is a five-inch continuous processing mixer manufactured by Teledyne Readco Company of York, Pa. The coolant passed through the processing mixer can be maintained at about 0° C. The temperature of the moisture-containing hydrogel 14 as it flows onto the exposed surface of the backing sheet 16 is important for controlling the infiltration of the coating into the backing sheet 16. The coolant will, under typical operating conditions, keep the extruded hydrogel 14 at a temperature of about 9° C. to 14° C. as it comes into contact with the backing 16. If deeper penetration is desired, the temperature of the hydrogel is lowered to about 9° C. for a typical hydrogel formulation. If less penetration is wanted, the temperature is raised closer to 15° C.

The hydrogel adhesive produced by the processing mixer, which is in a chilled fluid condition, is expelled onto backing sheet 16 and is spread out, e.g., by means of a knife coater of suitable known construction.

The backing 16 can be a porous or non-porous self-supporting sheet of water insoluble polymeric material that provides strength and integrity for the adhesive patch 10, and when porous can act as a substrate for receiving and retaining a portion of the adhesive hydrogel 14.

One preferred backing sheet 16 is a lightweight, pliable strip composed, for example, from a nonwoven fabric which consists of polymeric fibers such as polyester, cotton or cellulose fibers bonded together with a sizing resin. The backing sheet 16 should be nonirritating to human skin. If desired, the backing sheet 16 can be coated on its back surface with a release coating such as a silicone release coating as described in U.S. Pat. No. 4,696,854 which is incorporated herein by reference. One suitable release coating is a 100% solids electron beam curable silicone such as TEGO® Resin Acrylates/RC-Series RC 705 and RC 726 by Goldschmidt Chemical Corporation of Hopewell, Va. The preferred backing sheet 16 is a porous polymeric water insoluble nonwoven fibrous fabric. A suitable sizing material for bonding the fibers together is a latex resin.

The backing sheet 16 can comprise other stable, water insoluble flexible sheet materials. Another preferred backing comprises a 5.5 mil. strip of nonwoven fabric formed from a mixture of cellulose fibers derived from wood pulp and polyester fibers. The fibers are assembled loosely into the backing to maintain porosity. A sizing resin is applied to hold the fibers together. The sizing resin can comprise a nonirritating resin applied as a latex emulsion. One example is HYCAR® 26477, a resin produced by B.F. Goodrich Co. of Brecksville, Ohio. Another suitable backing sheet is a nonwoven fabric comprising a wetlay cellulose and polyester nonwoven fabric containing as a sizing an acrylic latex emulsion resin, e.g., product number N7601 by Dexter Corporation of Windsor Locks, Conn.

In another embodiment of the invention, the backing sheet 16 comprises a porous woven 5 mil. acetate polymer cloth sometimes known as "silk cloth." Another form of backing sheet 16 is an open-cell plastic foam strip of low density polyethylene or poly-vinyl acetate resin. Other backing sheets that can be used include woven cotton cloth or other cloth formed from a synthetic polymer. Suitable synthetic cloths include nylon, polyester, polyacetate. When the backing sheet 16 is a woven cloth, no sizing resin is needed. When the backing sheet 16 is pervious to air, the patch is non-occlusive to the skin. However, an occlusive backing can be used if desired.

In accordance with another optional form of the invention, the backing 16 is covered by a slippery friction-reducing layer 17 which has been broken away for clarity of illustration (FIG. 3), such as a sheet of slippery polyethylene, polytetrafluoroethylene (Teflon®), polypropylene, waxed parchment or any other slippery sheet material known to the art to reduce surface friction above the blister 8. Another alternative is to product the layer 17 by applying a slippery coating such as a silicone or wax-containing coating well known to those skilled in the adhesive tape art, which in ordinary adhesive tape serves as a release coating. If, for example, the slippery layer 17 is applied on the outer surface of the patches 10 shown in FIG. 2, the slippery surface characteristic will help reduce friction between the patch 10 and the stocking and shoe that are placed on the foot over the patch. In this way the low friction outer surface layer 17 of the patch 10 helps promote sliding contact and eliminate chafing between the patch 10 and a material such as an article of clothing that is placed over the patch 10.

After the hydrogel adhesive layer 14 has been applied to the backing 16, the patches can be formed by die-cutting, for example as described in U.S. Pat. No. 5,536,263.

Refer now to FIGS. 4 and 4A which illustrate a cross-sectional view of the patch after application to the skin 15 following removal of the liner sheet 18. As shown in the figures, the patch 10 has been applied over a blister 8. The blister 8 is covered by the stratum corneum 24 which may have, or may eventually develop, an opening 26 just above the center of the blister 8. When the opening 26 appears, fluid and necrotic tissue debris will flow out at an increasing rate to be absorbed into the hydrophilic adhesive layer 14 of the patch 10. If should also be noted that the moisture within the adhesive layer 14 soon hydrates the normally dry stratum corneum 24 (FIG. 4A), causing it to swell and to become more flexible. In addition, because of the added moisture, the free transport of fluids from the blister 8 upwardly into the hydrophilic adhesive gel 14 will be possible over an extended period of time as indicated by the vertical arrows in FIG. 4A. This osmotic effect is beneficial since it enhances drainage of the inflamed nodules. The evaporation of moisture through the porous backing 16 helps to maintain the osmotic differential and thus facilitates continued fluid transport out of the skin.

Figure 6:
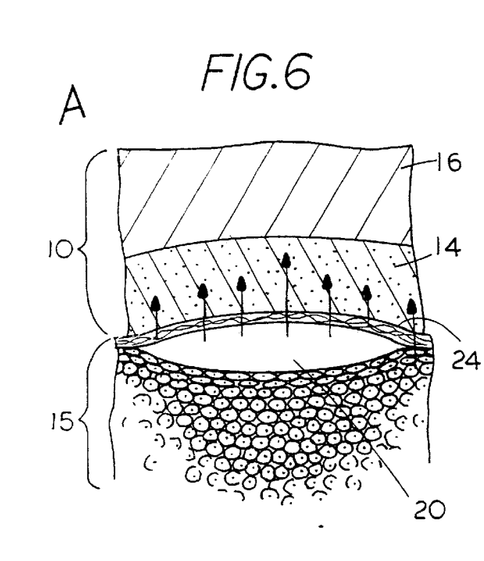
FIGS. 6A, 6B and 6C show sequential microscopic vertical cross-sectional views of the patch and underlying skin to illustrate the progressive improvement of a blister as an increasing amount of fluid diffuses from the blister and surrounding tissue into the hydrogel matrix of the patch.
Figure 6B:
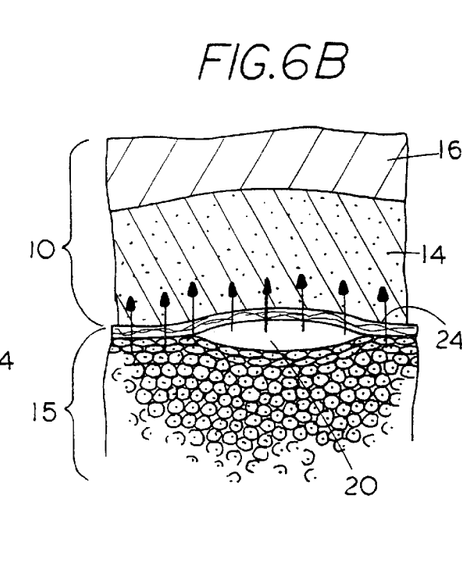
Figure 6C:
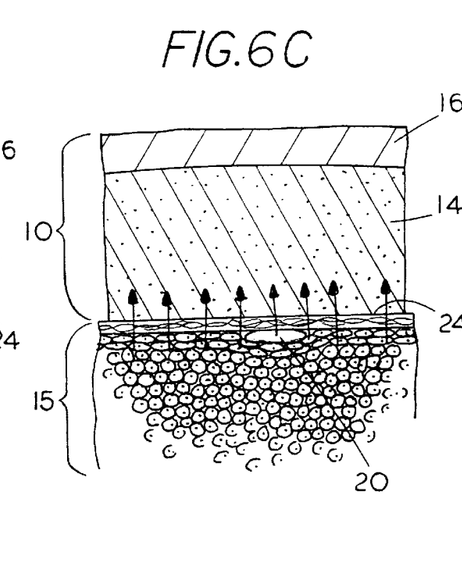

FIGS. 6A–6C show in timed sequence three microscopic vertical cross-sectional views of the same patch 10 and the underlying skin 15 to illustrate how an increasing amount of interstitial fluid from the blister 8 is progressively carried by osmotic pressure upwardly into the adhesive layer 14 of the patch 10, causing it to swell. These figures show the progressive improvement of the blister 8 over time proceeding from FIG. 6A to 6C as fluid is removed from the blister 8. The upward flow of fluid from the blister 8 into the adhesive layer 14 is indicated by vertical arrows in the figures. Finally, as shown in FIG. 6C, the blister 8 is much reduced as even more fluid is carried by osmotic pressure from the blister into the hydrophilic gel layer 14, thereby expanding the hydrophilic gel layer. When salt is used to create the hypertonic pressure within the adhesive 14, it provides an additional benefit in helping to keep the patch 10 sterile or at least helps to reduce the bacterial count to a safe level.

The invention will be better understood by reference to the examples. The patches are prepared by providing a porous nonwoven flexible fabric backing, e.g., nonwoven fabric having a thickness of 5 mils. To the flexible backing is applied a hydrophilic adhesive composition shown in each example to a thickness of about 3 mils. The hydrophilic adhesive compositions are given in the following examples:

EXAMPLES

Example 1

| Ingredient | % by Weight |
|---|---|
| Glycerin | 32.0 |
| Water | 10.0 |
| Propylene Glycol | 20.0 |
| Sodium Chloride | 1.0 |
| Polyquaternary amine | 37.0 |

Example 2

| Ingredient | % by Weight |
|---|---|
| Propylene Glycol | 33.0 |
| Water | 20.0 |
| Polyacrylamide | 15.0 |
| Sucrose | 11.0 |
| Maltodextrin | 12.0 |
| Tackifier comprising a vinyl acetate resin emulsion | 9.0 |

Example 3

| Ingredient | % by Weight |
|---|---|
| Water | 14.0 |
| Karaya | 10.0 |
| Albumin solids | 45.0 |
| Tackifier comprising an acrylic ester copolymer emulsion adhesive (B.F. Goodrich 26415) | 31.0 |

Example 4

| Ingredient | % by Weight |
|---|---|
| Water | 16.0 |
| Ethylene Glycol | 12.0 |
| Acrylic ester copolymer emulsion tackifier | 25.0 |
| Tackifier comprising vinyl acetate/dioctyl maleate copolymer emulsion | 38.0 |
| Polysodium acrylate | 9.0 |

Example 5

| Ingredient | % by Weight |
|---|---|
| Glycerol | 58.0 |
| Water | 10.0 |
| Polyacrylamide | 15.0 |
| Polyacrylic acid | 15.0 |
| Calcium chloride | 2.0 |

Example 6

| Ingredient | % by Weight |
| --- | --- |
| Propylene Glycol | 33.0 |
| Water | 20.0 |
| Polysulfonate | 15.0 |
| Sucrose | 11.0 |
| Maltodextrin | 12.0 |
| Tackifier comprising a vinyl acetate resin emulsion | 9.0 |

Example 7

| Ingredient | % by Weight |
| --- | --- |
| Propylene Glycol | 33.0 |
| Water | 20.0 |
| Carboxymethyl cellulose (CMC) | 15.0 |
| Sucrose | 11.0 |
| Maltodextrin | 12.0 |
| Tackifier comprising a vinyl acetate resin emulsion | 9.0 |

Example 8

| Ingredient | % by Weight |
| --- | --- |
| Propylene Glycol | 33.0 |
| Water | 20.0 |
| Carboxypropyl cellulose (CPC) | 15.0 |
| Sucrose | 11.0 |
| Maltodextrin | 12.0 |
| Tackifier comprising a vinyl acetate resin emulsion | 9.0 |

Example 9

| Ingredient | % by Weight |
| --- | --- |
| Glycerin | 49 |
| Nonionic and/or ionic polyacrylamide | 16 |
| Acrylic ester copolymer adhesive | 8 |
| Malto dextrin | 6 |
| Pectin | 4 |
| Deionized water | 6.6 |
| Proplylene glycol | 6.45 |
| Salicyclic acid | 2 |
| Sodium chloride | 1.95 |

Example 10

| Ingredient | % by Weight |
| --- | --- |
| Glycerin | 49 |
| Nonionic and/or ionic polyacrylamide | 16 |
| Acrylic ester copolymer adhesive | 8 |
| Malto dextrin | 6.25 |
| Pectin | 4 |
| Deionized water | 7 |
| Proplylene glycol | 7 |
| Salicyclic acid | 2 |
| Sodium chloride | 0.75 |

Example 11

A 48-year-old woman burned the distal palmer surface of the distal first four digits of the right hand by trying to move the metal grate on a gas stove which had unknowingly just been turned off. She suffered second degree burns on all of the four digits which all measured one centimeter across and one-half centimeter wide. All burned digits had fluid-filled blisters and the largest blister was on the index finger. All fingers were extremely painful. About one hour after the injury, one patch of Example 1 above was placed on each finger. Within five minutes the patient reported that the pain was completely gone. The patches were replaced about three hours after they were first placed. Examination of the fingers revealed there was no clinical fluid within the blisters, including the first digit. Further, with the blistered areas exposed, there was no recurrent pain to the air or gentle palpation. The examination of the patches revealed that all of the hydrophilic layers contained fluid and the layer on the index finger contained the most fluid. New patches were applied. The next day the patches were removed. There was minimal added fluid in the patches and no clinical blisters. The skin on the surface of the blistered areas was somewhat thickened but not painful to air or touch. The patches were not reapplied. When the burned areas were examined four days later, there were only minimal findings in the wounded areas. Further, the patient had never had any recurrence of pain or limitations of motion and use of the fingers. The probable action of the hypertonic hydrophilic gel layer of the patch on first and second degree burns is two-fold. First, the hypertonic gel layer removed the fluid within the blisters and some of the increased extracellular fluid in the surrounding areas as a result of the burn. The result of this action reduced the inflammation which apparently never returned, either by clinical action or by the subjective observation of the absence of pain. Second, the immediate effect of the hydrophilic gel almost immediately removed the pain by covering the burned surface with a moist layer of hydrogel, thereby reducing or eliminating the irritation to the pain sensors in the burned skin. As the fluid was removed and the acute inflammation subsided, the pain also clinically abated without the presence of the hydrogel patch.

The adhesive gels described above are applied to the backing 16 to provide a thin adhesive layer which is covered by a removable slip sheet or liner sheet 18 of any suitable commercially available composition. The patches 10 are then packaged in protective paper or plastic wrappers, pouches or envelopes for distribution. Also contained in the package, e.g., by being printed on the pouch or envelope, are directions for treating blisters by removing the liner sheet 18 and applying the patch to the skin directly over the blister. The user or health care worker can easily remove the patches from the envelope, remove the protective liner sheet, and apply the patch directly to the blister. The contact between the gel and the blistered skin consequently results in an osmotic gradient, pulling the fluid from the blister through the hydrated stratum corneum into the patch, thereby reducing fluid within the blister.

The patch 10 in accordance with the invention can be either non-sterile or, if desired, sterilized as described for example in U.S. Pat. No. 4,307,717 which is incorporated herein by reference.

If desired, any of the hydrophilic hydrogel adhesive compositions in accordance with the present invention can have dispersed therein one or more antimicrobial agents including but not limited to any of the following: isopropyl alcohol, povidone iodine, mercurochrome, hydrogen peroxide, benzoyl peroxide, retinoic acid, tetracycline, chlorohexidine gluconate, erythromycin, miconazole, acyclovir, isotretinoin, hexachlorophene, silver nitrate, acetic acid, salicylic acid and the like.

Many variations of the present invention within the scope of the appended claims will be apparent to those skilled in the art once the principles described herein are understood.

What is claimed is:

1. An adhesive patch comprising a backing and a hydrogel positioned on the backing wherein the hydrogel comprises a liquid, an adhesive, a thickening agent dispersed in the liquid, and a liquid-soluble solute dissolved in the liquid in sufficient quantity such that the osmotic pressure of the hydrogel is above about 308 mOsmol/L; such that when the adhesive patch is placed on skin above a blister, extracellular fluid contained in the blister is transported by osmotic pressure into the hydrogel thereby reducing accumulated extracellular fluid contained in the blister, while keeping the epidermis intact.

2. The adhesive patch of claim 1 wherein the backing comprises paper, cloth, plastic, open-cell polyurethane foam, open-cell polyethylene foam, nonwoven fabric, or a combination thereof.

3. The adhesive patch of claim 1 wherein the adhesive is a pressure sensitive adhesive.

4. The adhesive patch of claim 1 wherein the thickening agent is plant gum, polyacrylamide, acrylic acid, carboxymethyl cellulose, carboxypropyl cellulose, polyvinyl alcohol, kelp gum, karaya, starch, polyionic gel, polysodium acrylate, polyquaternary amine, polysulfonate, or a combination thereof.

5. The adhesive patch of claim 1 wherein the liquid-soluble solute is a carbohydrate, a soluble salt, a weak acid, a weak base, a monohydric alcohol, a polyhydric alcohol, a soluble amino acid, a liquid-soluble protein, or a combination thereof.

6. The adhesive patch of claim 1 wherein the liquid-soluble solute is sodium chloride, potassium chloride, calcium chloride, calcium carbonate, sucrose, glucose, levulose, lactose, acetic acid, adipid acid, aspartic acid, glutamic acid, malic acid, potassium bicarbonate, sodium bicarbonate, albumin, casein, glycine, alanine, cysteine, leucine, ethanol, methanol, glycerin, ethylene glycol, propylene glycol, or a combination thereof.

7. The adhesive patch of claim 1 wherein the liquid-soluble solute is present in about 0.1 wt % to about 15 wt.% of the hydrogel.

8. The adhesive patch of claim 1 wherein the hydrogel further comprises an antimicrobial agent.

9. The adhesive patch of claim 8 wherein the antimicrobial agent is isopropyl alcohol, povidone iodine, mercurochrome, hydrogen peroxide, benzoyl peroxide, retinoic acid, tetracycline, erythromycin, miconazole, acyclovir, chlorohexidine gluconate, hexachlorophene, silver nitrate, acetic acid, salicylic acid, isotretinoin, or a combination thereof.

10. A therapeutic biomedical adhesive hydrogel patch product for treating blisters of the skin, said product comprising:
an adhesive patch comprising a flexible backing, a pressure-sensitive hydrogel comprising an adhesive layer, liquid, a hydrophilic polymer dispersed in the liquid as a thickener and gel forming agent, and a biocompatible solute dissolved in the liquid;
the relative amounts of solute and liquid being adjusted such that the osmotic pressure of the hydrogel is above about 308 mOsmol/L, so as to maintain the adhesive hydrogel layer in a hypertonic state relative to the blister;
the adhesive layer having an exposed pressure-sensitive surface that, when placed in contact with the skin over the blister, hydrates the skin to create a hydrophilic bridge with the patient's skin which allows fluid transport between the blister and the patch across the hydrophilic bridge;
such that when the patch is placed on the skin above the blister, the fluid in the blister is transported by osmotic pressure into the hydrogel layer while keeping the epidermis intact and diminishing the acute accumulation of clear extracellular fluid between the epidermal and dermal layers of the skin, inflammation, infection, or pain produced by the blister.

11. The patch of claim 10 wherein the patch is contained in a package and the package includes written instructions for applying the patch to a blister by bonding the adhesive surface of the pressure-sensitive adhesive directly to the skin over the blister.

12. The patch of claim 10 wherein the solute is a member selected from the group consisting of a sugar, a salt, an acid, a base, an alcohol, an amino acid, and a protein.

13. The patch of claim 10 wherein the natural or synthetic polymer comprises a member selected from the group consisting of a plant gum, polyacrylamide, acrylic acid, carboxymethyl cellulose, carboxypropyl cellulose, polyvinyl alcohol, kelp gum, karaya, starch, polyionic gel, polysodium acrylate, polyquaternary amine, and polysulfonate.

14. The patch according to claim 10 wherein an antimicrobial agent is dispersed in the adhesive hydrogel layer.

15. The patch of claim 14 wherein the antimicrobial agent comprises a member selected from the group consisting of isopropyl alcohol, povidone iodine, mercurochrome, hydrogen peroxide, benzoyl peroxide, retinoic acid, tetracycline, erythromycin, miconazole, acyclovir, chlorohexidine gluconate, hexachlorophene, silver nitrate, acetic acid, salicylic acid and isotretinoin.

16. The patch of claim 8 wherein the patch has an exposed outer surface layer to promote sliding contact between the patch and an article over the patch.

17. The patch of claim 16 wherein the exposed outer surface layer comprises an ethylene polymer, polytetrafluoroethylene, a wax, or a silicone.

18. A method for treating a blister or burn comprising placing an adhesive patch over the blister or burn wherein the adhesive patch comprises a backing and a hydrogel positioned on the backing wherein the hydrogel comprises: liquid, an adhesive, a thickening agent dispersed in the liquid, and a liquid-soluble solute dissolved in the liquid in sufficient quantity such that the osmotic pressure of the hydrogel is above about 308 mOsmol/L; such that when the adhesive patch is placed on skin above a blister, extracellular fluid contained in the blister is transported by osmotic pressure into the hydrogel thereby reducing accumulated extracellular fluid contained in the blister, while keeping the epidermis intact.

19. The method of claim 18 wherein the liquid-soluble solute is sodium chloride, potassium chloride, calcium chloride, calcium carbonate, sucrose, glucose, levulose, lactose, acetic acid, adipid acid, aspartic acid, glutamic acid, malic acid, potassium bicarbonate, sodium bicarbonate, albumin, casein, glycine, alanine, cysteine, leucine, ethanol, methanol, glycerin, ethylene glycol, propylene glycol, or a combination thereof.

20. The method of claim 18 wherein the liquid-soluble solute is present in about 0.1 wt % to about 15 wt.% of the hydrogel.

21. The method of claim 18 wherein the treatment of the blister or burn comprises reducing swelling associated with blisters or burns, reducing inflammation associated with blisters or burns, reducing infection associated with blisters or burns, reducing pain associated with blisters or burns, or any combination thereof.

22. A therapeutic method of treating blisters of the skin for a human or animal, said method comprising:
providing a liquid-containing flexible patch having a hydrogel layer with an exposed surface for contact with the skin;
maintaining the osmotic pressure of the hydrogel above about 308 mOsmol/L; and
providing instructions for applying the liquid-containing hydrogel layer of the patch to the skin over the blister so that the surface forms a bridge with the patient's skin which allows fluid transport between the blister and the patch across the bridge so that fluid in the blister is then transported through the stratum corneum by osmotic pressure into the hydrogel layer while keeping the epidermis intact.

23. The method of claim 22 wherein a surface layer is applied to an exposed outer surface of the patch for promoting sliding contact between the patch and an article applied over the patch.

24. The method of claim 22 wherein an antimicrobial agent is dispersed in the hydrogel layer.

25. The method of claim 22 wherein the patch is applied to the skin to cover one or more blisters and an area of skin surrounding the blisters for reducing swelling, inflammation, infection, pain, or the acute accumulation of clear extracellular fluid between the epidermal and dermal layers of the skin.

26. The method of claim 22 wherein a tape or a cloth bandage is applied externally to the patch to further assist in securing the patch to the skin surface.

27. The method of claim 22 wherein the skin is at least partially hydrated by the patch and the hydrogel layer has a pressure-sensitive adhesive surface that bonds the patch to the skin.

28. The method of claim 22 wherein a sufficient amount of a nontoxic salt is dispersed in the adhesive layer to maintain a salt content greater than about 0.1% to 15% by weight of the adhesive.

29. A therapeutic method of treating blisters of the skin for a human or animal, said method comprising:
providing a flexible liquid-containing adhesive patch having an adhesive layer with an exposed pressure-sensitive surface for bonding to the skin,
maintaining the osmotic pressure of the adhesive layer above about 308 mOsmol/L; and
providing instructions for applying the liquid-containing adhesive patch to the skin over the blister so that the pressure-sensitive surface forms a bond with the skin to hold the patch in place on the skin and to hydrate at least an upper layer of the skin to form a hydrophilic bridge with the skin which allows fluid transport between the blister and the patch across the hydrophilic bridge so that interstitial fluid in and around the blister is then transported through the stratum corneum by osmotic pressure into the adhesive layer to diminish acute accumulation of clear extracellular fluid between the epidermal and dermal layers of the skin, inflammation, infection, or pain produced by the blister.

30. The method of claim 29 wherein an antimicrobial agent is dispersed in the adhesive hydrogel layer.

31. The method of claim 29 wherein the patch is applied to the skin to cover a blister for reducing swelling, inflammation, infection, pain, or the acute accumulation of clear extracellular fluid between the epidermal and dermal layers of the skin.

32. The method of claim 29 wherein a tape or a cloth bandage is applied to the patch to further assist in securing the patch to the skin surface.

33. The method of claim 29 wherein a sufficient mount of a nontoxic salt is dispersed in the adhesive layer to maintain a salt content greater than about 0.9% by weight of the adhesive.

34. The method of claim 29 including admixing a tackifying agent into the adhesive.

35. The method of claim 34 wherein the tackifying agent is a resin emulsion selected from the group consisting of a vinyl emulsion and an acrylic emulsion.

36. A therapeutic method of treating a first or second degree burn for a human or animal, said method comprising:
providing a liquid-containing flexible patch having a hydrophilic hydrogel layer with an exposed surface for contact with the burned skin,
maintaining the osmotic pressure of the hydrogel above about 308 mOsmol/L; and
providing instructions for applying the liquid-containing hydrophilic hydrogel layer of the patch to the skin over the burn so that the hydrophilic surface hydrates at least an upper layer of the patient's skin to form a hydrophilic bridge with the patient's skin which allows fluid transport between the burn and the patch across the hydrophilic bridge so that fluid in the burn is then transported through the stratum corneum by osmotic pressure into the hydrogel layer to improve or entirely relieve one or more of the symptoms produced by the burn.

37. The method of claim 36 wherein an antimicrobial agent is dispersed in the hydrogel layer.

38. The method of claim 36 wherein the patch is applied to the skin to cover one or more burns and an area of skin surrounding the burns for reducing swelling, inflammation, infection, pain, inflammation, or the acute accumulation of clear extracellular fluid between the epidermal and dermal layers of the skin.

39. The method of claim 36 wherein a tape or a cloth bandage is applied externally to the patch to further assist in securing the patch to the skin surface.

40. The method of claim 36 wherein the skin is at least partially hydrated by the patch and the hydrogel layer has a pressure-sensitive adhesive surface that bonds the patch to the skin.

41. The method of claim 36 wherein a sufficient amount of a nontoxic salt is dispersed in the adhesive layer to maintain a salt content greater than about 0.1% to 15% by weight of the adhesive.

42. The method of claim 36 wherein the salt content is from about 0.5% to about 7% by weight of the adhesive.

* * * * *

UNITED STATES PATENT AND TRADEMARK OFFICE
CERTIFICATE OF CORRECTION

PATENT NO. : 6,348,212 B1
DATED : February 19, 2002
INVENTOR(S) : Alan C. Hymes and Jane Nichols It is certified that error appears in the above-identified patent and that said Letters Patent is hereby corrected as shown below:

Column 8,
Line 9, Example 1, under "% by Weight", delete "32.0" and insert -- 22 --, therefor.

Column 14,
Line 13, delete "mount" and insert -- amount --, therefor.

Signed and Sealed this

Seventh Day of May 2002

Attest:

JAMES E. ROGAN
Attesting Officer   Director of the United States Patent and Trademark Office